United States Patent
Psarrakis et al.

(10) Patent No.: US 12,214,075 B2
(45) Date of Patent: Feb. 4, 2025

(54) APIXABAN SUSPENSION AND PREPARATION METHOD

(71) Applicant: PHARMA-DATA RESEARCH AND DEVELOPMENT SINGLE MEMBER S.A., Lavrio (GR)

(72) Inventors: Ioannis Psarrakis, Lavrion (GR); Konstantinos Lioumis, Lavrion (GR)

(73) Assignee: PHARMA-DATA RESEARCH AND DEVELOPMENT SINGLE MEMBER S.A., Lavrio (GR)

( * ) Notice: Subject to any disclaimer, the term of this patent is extended or adjusted under 35 U.S.C. 154(b) by 0 days.

(21) Appl. No.: 18/703,824

(22) PCT Filed: Oct. 25, 2022

(86) PCT No.: PCT/EP2022/079839
§ 371 (c)(1),
(2) Date: Apr. 23, 2024

(87) PCT Pub. No.: WO2023/072967
PCT Pub. Date: May 4, 2023

(65) Prior Publication Data
US 2024/0325306 A1 Oct. 3, 2024

Related U.S. Application Data

(60) Provisional application No. 63/272,407, filed on Oct. 27, 2021.

(30) Foreign Application Priority Data

Oct. 27, 2021 (NL) ...................................... 2029536

(51) Int. Cl.
| | | |
|---|---|---|
| A61K 9/10 | (2006.01) |
| A61K 9/00 | (2006.01) |
| A61K 31/4545 | (2006.01) |
| A61K 47/12 | (2006.01) |
| A61K 47/36 | (2006.01) |
| A61K 47/46 | (2006.01) |

(52) U.S. Cl.
CPC .............. *A61K 9/10* (2013.01); *A61K 9/0095* (2013.01); *A61K 31/4545* (2013.01); *A61K 47/12* (2013.01); *A61K 47/36* (2013.01); *A61K 47/46* (2013.01)

(58) Field of Classification Search
None
See application file for complete search history.

(56) References Cited

U.S. PATENT DOCUMENTS

2016/0143894 A1  5/2016  Khera et al.
2021/0299059 A1  9/2021  Liu et al.

FOREIGN PATENT DOCUMENTS

| CN | 109793715 A | 5/2019 |
| CN | 109010273 B | 3/2021 |
| EP | 1924291 A2 | 5/2008 |
| EP | 2900217 A1 | 8/2015 |
| WO | 2017182908 A1 | 10/2017 |
| WO | 2022123074 A1 | 6/2022 |

*Primary Examiner* — Robert A Wax
*Assistant Examiner* — Quanglong N Truong
(74) *Attorney, Agent, or Firm* — FISHERBROYLES, LLP; Roger L. Browdy

(57) ABSTRACT

The invention describes a buffered oral aqueous apixaban suspension comprising 0.08-0.20 w/v % micronized apixaban having a pH of 1.5-6.5 and a method for the preparation thereof.

20 Claims, 8 Drawing Sheets

5x 10x 20x 40x

APIXABAN SUSPENSION AND PREPARATION METHOD

Figure 1:
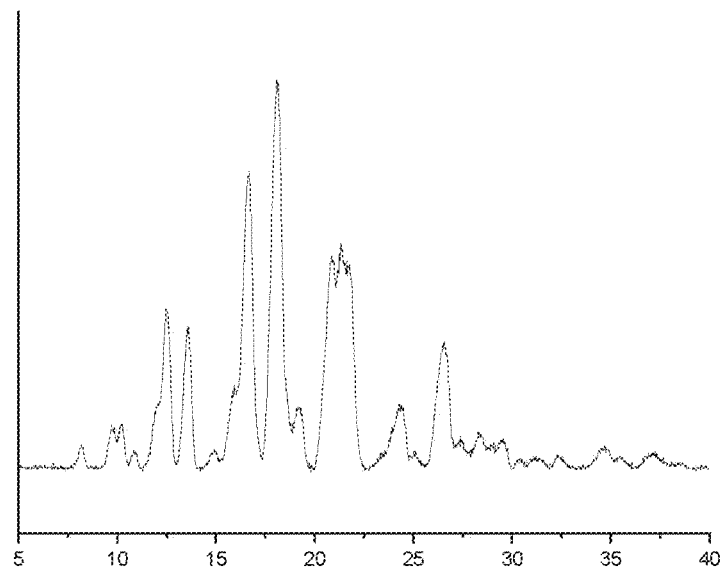
Figure 2:
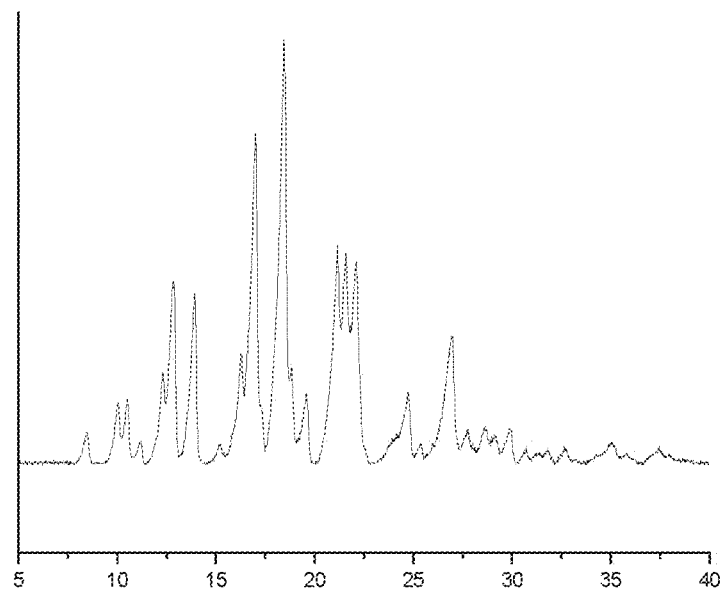
Figure 3:
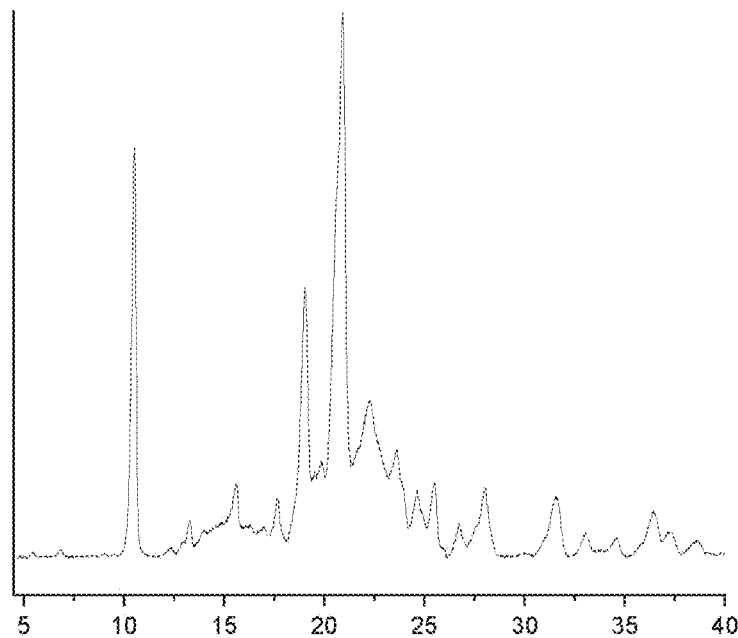
Figure 4:
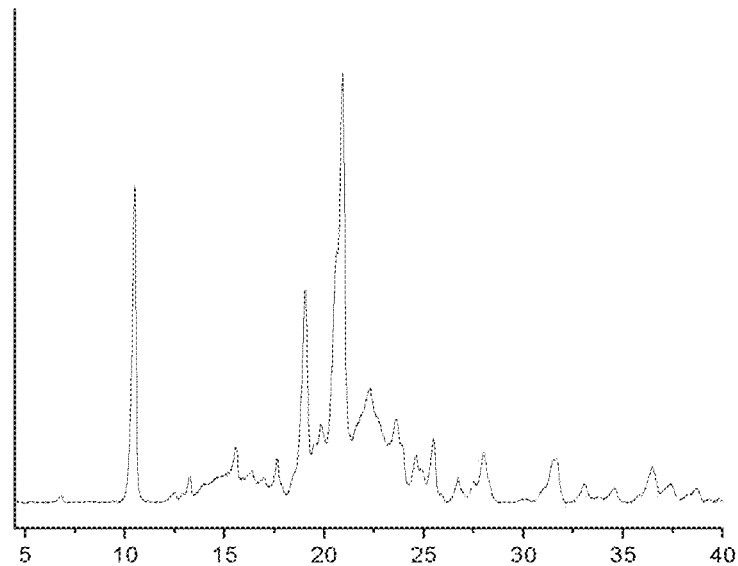
Figure 5:
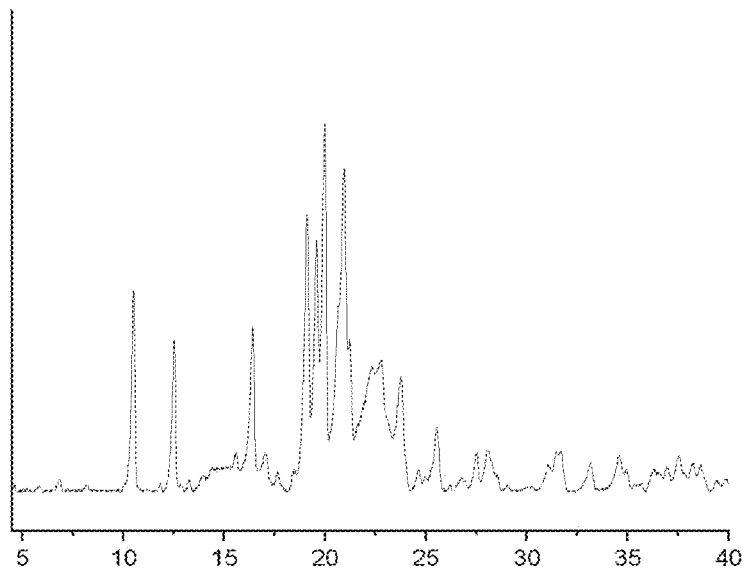
Figure 6:
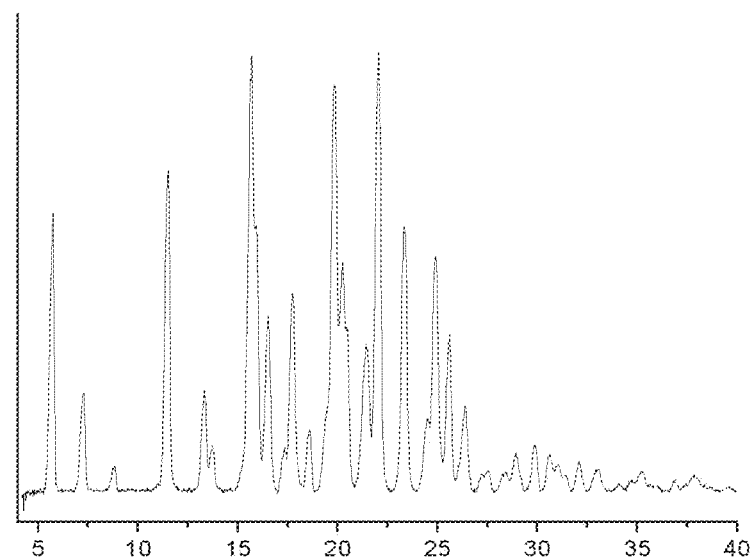
Figure 7:
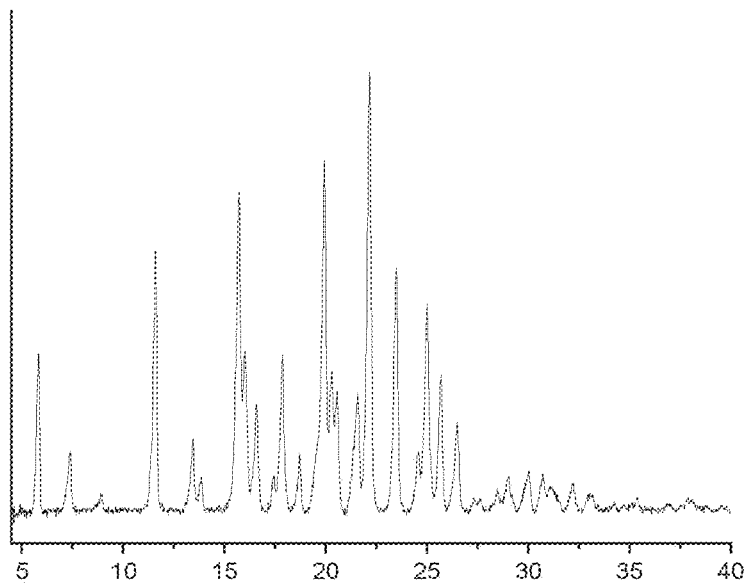
Figure 8:
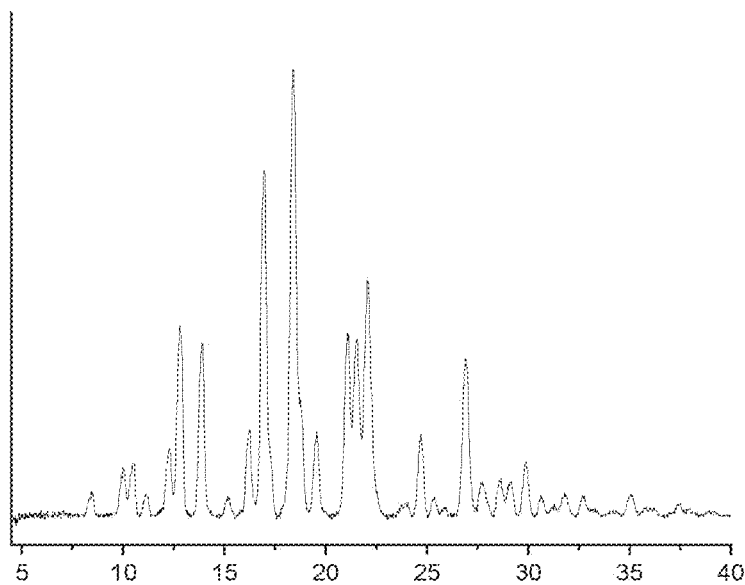
Figure 9:
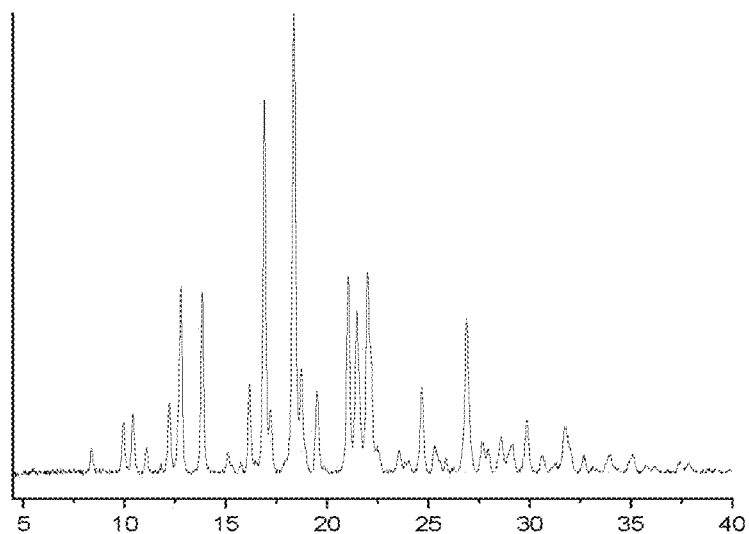

The invention relates to a stable buffered apixaban suspension and to a method for the preparation thereof.

Apixaban (CAS 503612-47-3, $C_{25}H_{25}N_5O_4$) is a pyrazolopyridine that is 7-oxo-4,5,6,7-tetrahydro-1H-pyrazolo[3,4-c] pyridine-3-carboxamide substituted at position 1 by a 4-methoxyphenyl group and at position 6 by a 4-(2-oxopiperidin-1-yl) phenyl group, having the following structural formula:

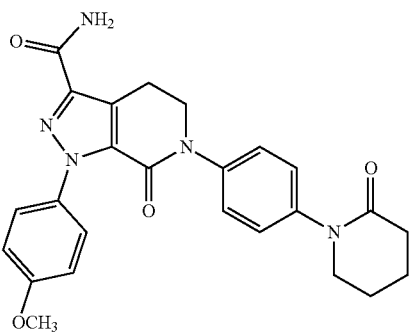 [SMILES: COc1ccc(-n2nc(C(N)=O)c3c2C(=O)N(c2ccc(N4CCCCC4=O)cc2)CC3)cc1]

Apixaban is a highly selective and reversible direct inhibitor of free and clot-bound factor Xa. Factor Xa catalyses the conversion of prothrombin to thrombin, the final enzyme in the coagulation cascade that is responsible for fibrin clot formation. Apixaban has no direct effect on platelet aggregation, but by inhibiting factor Xa, it indirectly decreases clot formation induced by thrombin an oral anticoagulant which helps prevent the formation of harmful blood clots. It prevents the formation of blood clots in the legs, lungs, brain, and heart. In the EU, apixaban is indicated for the prevention of venous thromboembolic events (VTE) in adults who have undergone elective hip or knee replacement surgery, the prevention of stroke and systemic embolism in adults with non-valvular atrial fibrillation (NVAF) with one or more risk factors, for the treatment of deep vein thrombosis (DVT) and pulmonary embolism (PE) in adults, and for the prevention of recurrent DVT and PE in adults.

The compound apixaban has been firstly described in EP1427415 and tablets are marketed under the trade name Eliquis by Bristol-Meyers Squibb and Pfizer.

Liquid preparations are known in the art. In order to provide a stable pharmaceutical liquid formulation for oral delivery, it is known to combine apixaban with an organic (co-) solvent, or to prepare a nano-emulsion where the particle size of apixaban is below 1000 nm. In all formulations for oral delivery emulsifiers are included as well.

EP2900217 describes such a liquid formulation comprising 20-30% water and over 30 w/w % of a polyhydric alcohol and an emulsifier. WO2022/123074 describes a pharmaceutical liquid formulation for oral delivery, wherein apixaban is a solution in polypropylene glycol. CN109010273A describes a nanosuspension of apixaban with improved solubility and dissolution rate, with a particle size of less than 1000 nm, further comprising an emulsifier. EP1924291 describes an injectable aqueous solution of neutral pH, comprising beta cyclodextrine as solubilizing agent. US2021/0299059 describes an injectable pharmaceutical composition comprising apixaban nanoparticles and an emulsifier.

WO2017/182908 describes a solid apixaban formulation, wherein a suspension of micronized apixaban in an aqueous solution of hydroxypropylcellulose and sodium lauryl sulphate is sprayed onto a carrier mixture followed by fluidised bed granulation. CN109793715A also describes an oral solid apixaban preparation, wherein a suspension of apixaban and hypromellose is subjected to wet granulation.

It has now surprisingly been found that buffered aqueous suspensions of micronized apixaban having an acid pH has advantageous physicochemical properties rendering such suspensions very suitable for oral administration. The suspensions of the invention thereto comprise 0.08-0.20 w/v % micronized apixaban and have a pH of 1.5-6.5. The suspensions of the invention are form stable, have good dissolution profiles and have a good stability, i.e. low impurity formation in time. The term 'form stable' herein means that the crystal form of the apixaban in the suspension is not significantly converted to another form, or from a crystal form to the amorphous form or vice versa. It was further found that a micronized apixaban suspension in an aqueous buffer of the invention was stable even in absence of an emulsifier, surfactant, dispersant or solubiliser. Indeed, a true suspension is a heterogenous mixture of a liquid (in casu water) containing solid particles that not have settled. In contrast, a dispersion is a biphasic system in which distributed particles of one material are dispersed in a continuous phase of another material. An emulsion is a such a system wherein the two liquid phases are immiscible; by the presence of an emulsifier, one of the phases (discontinuous phase) can be present as droplets in the other continuous phase. The apixaban suspension of the present invention appears to be a true suspension, i.e. particles suspended in a continuous liquid phase without the need for an emulsifier, surfactant, dispersant, or solubiliser.

The term 'oral suspension' means a pharmaceutical liquid suspension for oral delivery.

The term 'aqueous' herein means that the suspension comprises at least 70 w/w % water, in particular in particular at least 75 w/w %, preferably at least 80 w/w % water, more preferably at least 85 w/w %, even more preferably at least 90 w/w %, and most preferably at least 95 w/w %, 96 w/w % or 97 w/w %.

The term 'micronized' means that the apixaban for the suspension has a particle size $D_{90}$ of 20 μm or less, preferably of 15 μm or less, most preferably of 10 μm or less. Further, the term 'micronized' will be understood by the skilled person to exclude nanoparticles, i.e. below 0.5 nm, preferably below 700 nm, or 800 nm and more preferably below 1000 nm. To this end, the micronized apixaban preferably has a $D_{10}$ of at least 0.9 μm, preferably of at least 1.0 μm, most preferably of at least 1.1 μm. The D50 is preferably at least 3 μm, more preferably 3-5 μm. The D3,2 is preferably at least 2 μm, more preferably 2-4 μm, most preferably 2-3 μm. The D4,3 is preferably at least 4 μm, more preferably 4-6 μm, most preferably 4-5 μm. The skilled person is aware as to how to obtain a suspension with the said envisaged particle sizes, and can e.g. be obtained by low or medium speed homogenisation. High speed homogenisation that would result in a nanosuspension, i.e. in apixaban nanoparticles to to be avoided.

It has been found that micronized apixaban in an amount of 0.08-0.20 w/v % keeps its crystalline or amorphous structure without changing to another solid form at buffered acid pH. The amount is preferably 0.10-0.15 w/v %.

The structure of apixaban in the suspension can be amorphous or crystalline. Different crystalline structure structures of apixaban are known (Forms I-X, Barbas et al., Mol. Pharmaceutics 2018, 15, 5, 1909-1916), forms A, B, C (IN2013MU02771A), form a and H3 (EP2752414), form gamma (CN105037349), forms I-V and amorphous (CN103539795, forms N-1, H-2 and alpha (Solanki, World J. Pharm. Sci. 2015, 3 (3): 663-677). Form I is the pharmaceutically active ingredient of the known pharmaceuticals such as Eliquis. Preferably, at least 95% w/w % of the apixaban present in the suspension is in crystalline Form I, more preferably at least 96 w/w %, even more preferably at least 98 w/w % and most preferably at least 99 w/w % if not all.

The form stability is improved at acid pH, i.e. between 1.5 and 6.5. The pH is preferably between 3.0-5.0, more preferably 3.5-4.5, and most preferably 3.7-4.3.

The suspension is buffered. The term 'buffer' is known in the art and a skilled person is well capable of providing a suitable buffer. A buffering agent can advantageously be provided by a weak acid and its conjugate base, or a weak base with its conjugate acid. The suspension therefore preferably comprises one or more buffering agents, preferably in an amount of 0.05- 2.0 w/w %, more preferably 0.5-1.0 w/v %. The skilled person is aware of suitable buffering agents and systems. In an attractive embodiment, the buffering agents may comprise any of the group, consisting of hydrochloric acid, acetic acid, ammonia solutions, monoethanolamine, diethanolamine, triethanolamine, meglumine, sodium citrate, citric acid, lactic acid, phosphoric acid, propionic acid, sulphuric acid, tartaric acid, potassium bicarbonate, potassium citrate, potassium hydroxide, sodium bicarbonate, sodium borate, and sodium hydroxide. The one or more buffering agents preferably comprise citric acid, preferably anhydrous, and a citrate salt, preferably sodium citrate, more preferably sodium dihydrate citrate.

The stability of the suspension is further improved by the presence of one or more thickening agents, preferably in an amount of 0.15-0.5 w/v %, more preferably 0.2-0.3 w/v %. The skilled person is aware of suitable thickening agents. In an attractive embodiment, the one or more thickening agents are chosen from the group, consisting of xanthan gum, acacia, guar gum, locust bean gum, gum tragacanth, gelan gum, hydroxyethyl cellulose, hydroxypropyl cellulose, sodium alginate, sodium carboxy methylcellulose, starch, carbopols, methylcellulose, polyethylene oxide polymer and combinations thereof, the thickening agent preferably being xanthan gum. In a very attractive embodiment, the thickener comprises xanthan gum, preferably in an amount of 0.20-0.30 w/v %.

For improved microbial efficacy, the oral aqueous suspension of the invention preferably comprises one or more preservatives, preferably in an amount of 0.01-0.40 w/v %, more preferably in an amount of 0.02-0.10 w/v %. The skilled person is aware of suitable preservatives, in particular those that are effective in the acid range. In an attractive embodiment, the one or more preservatives are chosen from the group, consisting of benzoic acid, sodium benzoate, potassium sorbate, benzyl benzoate, benzalkonium chloride, benzethonium chloride, boric acid and salts thereof, cetrimide, chlorocresol, thimerosal, imidurea, glycerine, monothioglycerol, propylene glycol, propionic acid and salts thereof, acetic acid and salts thereof, lactic acid and salts thereof, alkyl acids like sorbic acid and salts thereof, pentetic acid and salts thereof, sodium sulphite, sodium metabisulphite, benzyl alcohol, ethylalcohol, potassium sorbate, methyl paraben, ethyl paraben, propyl paraben, butyl paraben, and combinations thereof. The one or more preservatives preferably comprise benzoic acid and/or sodium benzoate, in particular 0.02-0.10 w/v %.

For an even more improved stability, the oral suspension of the invention preferably comprises one or more antioxidants, preferably in an amount of 0.01-2.5 w/v %, more preferably in an amount of 0.5-1.0 w/v %. The skilled person is aware of suitable antioxidants. The antioxidant is preferably chosen from the group, consisting of sodium metabisulphite, sodium sulphite, sodium thiosulfate, propyl gallate, butylated hydroxyl anisole, butylated hydroxyl toluene, tocopherol, ascorbyl palmitate, ascorbic acid and combinations thereof. The antioxidant preferably comprises sodium metabisulphite or propylgallate.

To improve the taste of the suspension, and therewith the patient compliance, the oral suspension preferably comprises one or more sweetening agents. The one or more sweetening agents are preferably present in an amount that corresponds with the sweetening power of 60-600 w/v % saccharose. This means that, e.g., in case sucralose is used as the sole artificial sweetening agent, the amount of sucralose is 0.1-1.0 w/v %, as the sweetening power of sucralose is 600 times that of saccharose. More preferably, the amount of non-sugar alcohol sweetening agent in the solution has a sweetening power that corresponds with the sweetening power of 100-300 w/v % saccharose.

Preferably, the one or more sweetening agents are present in the suspension in an amount of 0.1-10 w/v %. The one or more sweetening agents are preferably artificial sweetening agents, preferably chosen from the group consisting of sucralose, sodium saccharin, aspartame, alitame, acesulfame-K, cyclamate, stevioside, glycyrrhizin, neohesperidin, dihydrochalcone, thaumatin, and combinations thereof. The one or more sweetening agents preferably comprise sucralose and/or sodium saccharin, preferably in an amount of 0.3-1.0 w/v %, more preferably 0.4-0.8 w/v %, the weight ratio between sucralose and sodium saccharin preferably being 1:0.3-0.5.

To improve the taste of the suspension, and the patient compliance even more, the oral suspension of the invention preferably comprises one or more flavouring agents. The suspension preferably comprises 0.05-0.2 w/v % flavouring agent. The skilled person is aware of suitable flavouring agents. to this end, the flavouring agent is selected from the group consisting of peppermint, spearmint, *eucalyptus*, vanilla, forest fruits flavour, grapefruit, orange, lime, lemon, mandarin, pineapple, strawberry, raspberry, mango, passion fruit, kiwi, 10 apple, pear, peach, apricot, cherry, grapes, banana, cranberry, blueberry, black currant, red currant, gooseberry, lingonberries, cumin, thyme, basil, camomile, valerian, fennel, parsley, tarragon, lavender, dill, bergamot, *salvia*, aloe vera balsam and combinations of two or more thereof. The one or more flavouring agents preferably comprise peppermint or vanilla flavour.

In alternative attractive embodiments, the oral suspension further comprises one or more pharmaceutically acceptable excipients, selected from the group consisting of dispersants, chelating agents, surfactants, wetting agents, colouring agents, and combinations thereof.

The dispersion preferably comprises one or more chelating agents. The skilled person is aware of suitable chelating agents. Preferably, the chelating agent comprises EDTA, the chelating agent preferably being present in the suspension in an amount of 0.01-1.0 w/v %, more preferably in an amount of 0.05-0.5 w/v %, most preferably in an amount of 0.08-0.12 w/v %.

The suspension is preferably void of a dispersant. The presence of a dispersant usually improves the even distribution of the particles throughout the suspension and may avoid undesired debris formation, rendering manual shaking before use not or to a lesser extent, the inclusion of such a dispersant has shown not to be necessary in the suspension of the invention for an even particle distribution without debris formation necessary.

The suspension of the invention is also preferably void of an emulsifier, and/or a surfactant, and/or a solubiliser, such as a cyclodextrine.

Although not necessary, one or more co-solvents can be included in the suspension. e.g. to decrease the formation of impurities during storage. If present, the amount of co-solvent is preferably between 1 and 20 w/v %, more preferably 2-10 w/v %.

If present, the co-solvent is preferably a water miscible organic solvent, and preferably chosen from the group, consisting of glycerol, acetone, alcohol, benzyl alcohol, benzyl benzoate, butylene glycol, dibutyl phthalate, diethyl phthalate, dimethyl phthalate, dimethyl sulfoxide, dimethylacetamide, glycofurol, isopropyl alcohol, isopropyl myristate, isopropyl palmitate, polyethylene glycol, propylene carbonate, pyrrolidone, triacetin, triethyl citrate and triolein. The co-solvent preferably comprises glycerol, more preferably in an amount of 0.3-0.7 w/v %.

Preferably, at least 98 w/w % of the solid form of apixaban in the suspension is still present after storage of 30 ml of the suspension for 10 months in a closed 30 ml amber glass vial at 25° C., 60% humidity in the dark. This is in particular valid for form I.

The invention also relates to the use of micronized apixaban as defined herein for the preparation of an oral suspension as defined herein.

The invention also provides a dry powder composition for constitution of the buffered oral aqueous apixaban suspension of the invention, comprising: micronized apixaban, sweetener, flavour, preservative, antioxidant, chelating agent, thickener, and buffering agent, where the components are preferably as defined herein as defined herein, both as compounds and as amounts. The powder is free from a dispersant, a surfactant, an emulsifier and preferably free from a solubiliser.

The dry powder of the invention preferably comprises a bulking agent, the bulking agent preferably being chosen from: calcium carbonate, calcium lactate, calcium phosphate, in particular dibasic anhydrous, dibasic dihydrate or tribasic calcium phosphate, calcium sulphate, cellulose, in particular microcrystalline, powdered, or silicified microcrystalline cellulose, cellulose acetate, starch, in particular corn starch or pregelatinized starch, dextrates, dextrin, dextrose, erythritol, isomalt, kaolin, lactitol, lactose, in particular anhydrous lactose lactose monohydrate, corn starch lactose monohydrate, microcrystalline cellulose lactose monohydrate or povidone lactose, monohydrate and powdered cellulose lactose, spray-dried, magnesium carbonate, magnesium oxide maltodextrin, mannitol, polydextrose, sodium chloride, sorbitol, sucrose, confectioner's sugar spheres, talc, xylitol, most preferably being sorbitol.

The dry powder of the invention further preferably comprises a lubricant, chosen from calcium stearate, magnesium stearate, myristic acid, palmitic acid, potassium benzoate, sodium benzoate, sodium stearyl fumarate, stearic acid, talc and zinc stearate.

The invention related to the use of a dry powder as defined above for the preparation of a suspension of the invention, and to the said dry powder for use in the preparation of such a suspension.

In an attractive embodiment, the dry powder of the invention comprises
- 0.1-0.15 w/w % micronized apixaban,
- 0.5-1.8 w/w % buffering agent,
- 0.10-0.60 w/w % thickener,
- 0.005-0.50 w/w % preservative,
- 0.06-1.4 w/w % sweetener, and
- 0.03-0.3 w/w % flavouring agent, as defined herein.

Examples of such dry compositions are given below in table 1.

TABLE 1

Dry compositions in g.

| Composition 1 | | Composition 2 | | Comparative Composition 1 | |
|---|---|---|---|---|---|
| Apixaban | 0.125 | Apixaban | 0.125 | Apixaban | 0.125 |
| sucralose | 0.45 | sucralose | 0.45 | sucralose | 0.45 |
| pepermint flavor | 0.1 | pepermint flavor | 0.1 | pepermint flavor | 0.1 |
| Na benzoate | 0.06 | methyl paraben Na | 0.2 | methyl paraben Na | 0.2 |
| Na metabisulfite | 0.8 | xanthan gum | 0.2 | xanthan gum | 0.2 |
| EDTA | 0.1 | citric acid anhydrous | 0.18 | citric acid anhydrous | 0.18 |
| xanthan gum | 0.2 | sodium citrate | 0.3 | sodium citrate | 0.3 |
| citric acid anh. | 0.3 | sorbitol SD | 2 | Poloxamer 188 | 1 |
| sodium citrate | 0.38 | total | 3 | sorbitol SD | 2 |
| sorbitol SD | 2 | | | total | 5 |
| total | 4.515 | | | | |

In another aspect of the invention, a method for the preparation of a buffered oral aqueous apixaban suspension as described above is provided, comprising the steps of:
(i) providing purified water,
(ii) if present, admixing the preservative,
(iii) if present, admixing the sweeteners
(iv) if present, admixing the antioxidant,
(v) if present, a chelating agent,
(vi) admixing the pH buffer agent,
(vii) if present, admixing the flavour,
(viii) admixing the apixaban to the mixture of steps (i)-(vii) and homogenise
(ix) if present, admixing the thickener and homogenise
(x) if present, admixing the dispersant and/or the co-solvent,
(xi) if necessary, adjust pH at 1.5-6.5 with ingredients of step (v),
(xii) if necessary, adjust to the final volume by adding purified water, (xiii) optionally, filter through a 10 μm pore sieve or higher, and (xiv) filling into an appropriate container.

Steps (ii)-(vii) can be performed in any sequence. To the obtained mixture, apixaban is admixed followed by homogenisation. Preferably, thickening agent is then added, followed by another homogenisation step. If present dispersant and/or co-solvent is subsequently added, but as described above, the suspension is preferably void of dispersant and also attractively also void of a co-solvent. Thereafter, the pH is adjusted, and the volume is adjusted to the envisaged final volume with purified water. After an optional step of filtration, the suspension is filled into a light protected container, such as an amber glass vial.

In still another embodiment, the invention relates to the preparation of a dry powder composition for a buffered oral aqueous apixaban suspension as described above, comprising the steps of:

(i) combining the apixaban, the pH buffer agents, the flavour, the thickener, the sweetener, and, if present, bulking agent,, antioxidant, chelating agent, (ii) mixing the ingredients of step (i)

(iii) if present, admixing lubricant, followed by mixing (iv) optionally, sieving, and (v) filling into an appropriate container.

EXAMPLES

The process was performed using regular manufacturing equipment. The basic steps are as follows:

Materials and methods

Preparation of colchicine solutions compositions

The following ingredients were used in the preparations described below:

Apixaban (Neuland Labs., India; Amino Chemicals, Malta; Teva, Israel);
Sucralose (Nutrilo, Germany)
Peppermint flavour (Givaudian, Switzerland)
Vanilla flavour (Symrise, Germany)
Glycerol (glycerine 4808, 99.5%, Oleon NV, Belgium)
Methyl paraben sodium (Emprove®, Merck, US)
Propyl paraben sodium (Clariant, Germany)
Sodium benzoate (Ganesh Benzoplast, India)
Metabisulphite sodium (Merck, Germany)
Disodium edetate salt (EDTA), Scl ITALIA, Italy.
Saccharin sodium (JMC Corporation, Japan)
Xanthan Gum (Jungbunzlauer, Switzerland)
Hydroxyethylcellulose (Natrosol 250 HX®, Ashland, US)
Polysorbate 80 (Mosselman SA, Belgium)
Sodium alginate (Manukol LKX, DuPont, USA)
Citric acid anhydrous (Citrique Belge, Belgium)
Trisodium citrate dihydrate (Jungbunzlauer, Switzerland)
Propyl gallate (Panreac Applichem, Germany)
Sorbitol spray dried powder (SPI Pharma, US)
Poloxamer 188 powder (BASF, Germany)

Formulas 2.1-2.1.1 as given in table 2 are suspensions and were prepared as follows.

For a batch size of 100 ml, the preservative was added to about 94 to 98 g of purified water depending the formula. Either 0.2 g of methyl paraben sodium and 0.018 g propyl paraben sodium, or sodium benzoate 0.06 g were mixed to purified water until complete dissolution.

Then 0.45 g of sucralose and 0.2 g of saccharin sodium were added to the above solution and mixed until complete dissolution.

After the buffers are added, citric acid anhydrous (depending the formula 0.18-0.3 g) and sodium citrate dihydrate (0.3-3.5 g, depending on the formula) to the above solution and mixed until complete dissolution.

Subsequently, the antioxidants are added 0.8 g of sodium metabisulfite and 0.1 g of EDTA to the above solution and mixed until complete dissolution.

0.1 g of peppermint flavour or 0.1g of vanilla cream flavour are then added and mixed until a clear solution is formed.

Then, 0.125 g of micronized apixaban (D90 of ≤10 μm) is added. A suspension is created and dispersed well using a laboratory homogeniser (X1000D Unidrive, CAT, Germany) for 3-10 minutes, preferably 2-5 minutes in a speed range of preferably 4300-7000 rpm.

Then, the thickening agent is added. As thickening agent, either 0.23 g of xanthan gum or 0.2 g of hydroxyethyl cellulose or 0.4 g of sodium alginate were added and dispersed well using the above homogeniser for 2-5 minutes in the indicated speed range.

If present, 5 g of glycerol as cosolvent is then admixed.

Final mixing was performed for 10-20 minutes in order to create an homogeneous white suspension.

The suspension was filtered through a 10-20 μm sieve and filled in type III amber glass vials.

Dry formulas 1-3 as given in table 1 are powders for oral suspensions and were prepared as follows.

For a batch size of 100 ml liquid product, 0.125g of apixaban micronized along with the below ingredients are weighted and passed through appropriate sieve of 16 mesh:

2 g sorbitol SD
0.2 g xanthan gum
1 g poloxamer 188 (optionally)
0.3-0.38 g of sodium citrate dihydrate
0.18-0.30 g of citric acid anhydrous
0.2 g paraben methyl sodium (optionally)
0.1 g peppermint flavour
0.45 g sucralose
0.8 g sodium metabisulfite (optionally)
0.1 g EDTA (optionally)
0.06 g sodium benzoate (optionally)

The above ingredients are mixed all together for 5-10 minutes

A lubricant can be optionally added in a concentration of 0.1-1%, followed by another mixing for 2-3 minutes The mixture is then filled into a glass bottle of 100 ml volume or in a sachet.

Analytical procedures
Instrumentation
Chromatographic System: Shimadzu 2030C 3D Plus
Detector: Photodiode Array
Column: Agilent Zorbax XDB-C18 (150×4.6 mm, 3 μm)
Reagents and solvents
Ultrapure Water, conductivity 18.2 μΩ/cm (MilliQ purification apparatus, Millipore Direct-Q UV)
Acetonitrile HPLC grade
Acetic acid
Ammonium Acetate
Chromatographic Parameters
Mobile Phase A: 0.03 M ammonium acetate pH (4.7±0.05)
Mobile Phase B: Acetonitrile: Water 90:10 (v/v), acidified with 1.0 ml acetic acid
Injection Volume: 10.0 μL
Elution: Gradient elution
Wavelength: 240 nm
Column temperature: 20° C.
Flow rate: 0.8 ml/min
Run Time: 20 min
Retention Time of apixaban: 3.5 min

TABLE 2

| Apixaban 2.5 mg/2 ml oral suspension | function | Formula 2.1 | Formula 2.1PS | Formula 2.1.1 | Formula 2.2 | Formula 2.3 | Formula 2.4 | Formula 2.5 | Formula 2.6 | Formula 3 | Formula 4 | Formula 5 |
|---|---|---|---|---|---|---|---|---|---|---|---|---|
| Composition of samples (w/v %) | | | | | | | | | | | | |
| Apixaban (Neuland) | active substance | 0.125 | 0.125 | 0.125 | 0.125 | 0.125 | 0.125 | | 0.125 | 0.125 | 0.125 | 0.125 |
| Apixaban (Amino) | active substance | | | | | | | 0.125 | | | | |
| Sucralose | sweetener | 0.45 | 0.45 | 0.45 | 0.45 | 0.45 | 0.45 | 0.45 | 0.45 | 0.45 | 0.45 | 0.45 |
| Peppermint flavour | flavour | 0.1 | 0.1 | | 0.1 | 0.1 | 0.1 | 0.1 | 0.1 | 0.1 | 0.1 | 0.1 |
| Vanilla flavour | flavour | | | 0.1 | | | | | | | | |
| Glycerol | solvent | | | | | | | | | | 5.000 | |
| Methyl paraben sodium | preservative | 0.2 | 0.2 | 0.2 | 0.2 | 0.2 | | 0.2 | 0.2 | 0.2 | 0.2 | 0.2 |
| Propyl paraben sodium | preservative | 0.018 | 0.018 | 0.018 | 0.018 | 0.018 | | 0.018 | 0.018 | 0.018 | 0.018 | 0.018 |
| Na benzoate | preservative | | | | | | 0.06 | | | | | |
| Na metabisulfite | antioxidant | | | | 0.8 | 0.8 | 0.8 | | | | | |
| EDTA | chelating agent | | | | 0.1 | 0.1 | 0.1 | | | | | |
| Saccharin sodium | sweetener | 0.2 | 0.2 | 0.2 | 0.2 | 0.2 | 0.2 | 0.2 | 0.2 | 0.2 | 0.2 | 0.2 |
| Xantan gum FF | thickener | 0.23 | 0.23 | 0.23 | 0.23 | 0.23 | 0.23 | 0.23 | 0.23 | | 0.23 | |
| Hydroxy ethyl cellulose | thickener | | | | | | | | 0.2 | | | |
| Sodium alginate | thickener | | | | | | | | | | | 0.4 |
| Polysorbate 80 | dispersant | | 0.2 | | | | | | 2.0 | | | |
| Citric acid anhydrous | buffer | 0.18 | 0.18 | 0.18 | 0.18 | 0.05 | 0.3 | 0.18 | 0.18 | 0.18 | 0.18 | 0.18 |
| Trisodium citrate 2•H$_2$O | buffer | 0.3 | 0.3 | 0.3 | 0.95 | 3.5 | 0.386 | 0.3 | 0.3 | 0.3 | 0.3 | 0.3 |
| Purified water | solvent | 98.2 | 98.2 | 98.2 | 96.7 | 94.3 | 97.3 | 98.2 | 98.2 | 98.3 | 93.2 | 98.1 |
| Total | | 100.003 | 100.003 | 100.003 | 100.053 | 100.073 | 100.051 | 100.003 | 100.003 | 100.073 | 100.003 | 100.073 |
| pH | | 5.5 | 5.5 | 5.5 | 5.5 | 6.5 | 4 | 5.5 | 5.5 | 5.5 | 5.5 | 5.5 |

TABLE 3

Gradient Elution Program for the determination of Apixaban (Assay)

| Time (min) | Mobile Phase A (%) | Mobile Phase B (%) |
|---|---|---|
| 0.01 | 55 | 45 |
| 5.00 | 55 | 45 |
| 10.00 | 20 | 80 |
| 12.00 | 55 | 45 |
| 20.00 | 55 | 45 |

Preparation of Buffer 2.31 g of ammonium acetate are weighed in a 1000 ml beaker and dissolved with water. The pH of the solution is adjusted to (4.7+0.05) with acetic acid. The solution is transferred to a volumetric flask and diluted till the mark with water. The buffer solution is filtered through 0.22 µm filter paper.

Diluent (blank solution): acetonitrile: water (50:50), (v/v).

Apixaban stock solution: 12.5 mg of Apixaban reference standard are weighed into a 25 ml volumetric flask and dissolved till the mark with diluent. The concentration of apixaban stock solution is 500 mg/L.

Standard Working Solution: 0.625 ml of the stock solution are transferred into a 25 ml volumetric flask and diluted till the mark with diluent. The concentration of apixaban working solution is 12.5 mg/L.

Oral solution Test Solution: Apixaban oral solution samples are stirred, using a magnetic stirrer for 30 minutes. During this period, the samples are shaken vigorously manually every five minutes, 1.0 ml of Apixaban oral solution is weighed into a 10 ml volumetric flask and diluted to volume with diluent (Solution A). Consequently, 0.1 ml of the diluted test solution is transferred into a 2 ml glass vial and diluted till 1.0 ml with diluent (Solution (B), final concentration 12.5 mg/L). 10 µL of solution (B) is injected in the HPLC system. The quantification of apixaban in oral solution is conducted using a 12.5 mg/L standard solution (one-point calibration). All samples are prepared in duplicates, and labeled as OralTest solution 1 and OralTest solution 2, respectively.

The Sequence for the determination of apixaban is presented on Table 4.

TABLE 4

Sequence for the determination of Apixaban (Assay)

| Sample Description | Number of injections |
|---|---|
| Diluent | 1 |
| Apixaban Working Standard | 6 |
| Apixaban Working Standard_2 | 2 |
| Oral Test Solution 1 | 1 |
| Oral Test Solution 2 | 1 |

Calculation of the % content of apixaban by equation:

$$\% \text{ Apixaban} = \frac{A_{smp} * V_{smp} * W_{std} * P_{std} * D_{std} * 100}{A_{std} * W_{smp} * LC * D_{smp} * V_{std}}$$

wherein: Asmp is the peak area response of active substance in the sample solution chromatograms; $A_{std}$ is average peak area response of active substance in the standard solution chromatograms; $W_{smp}$ is the weight of the test substance in mg; $W_{std}$ is the weight of the active substance in standard in gr.; $V_{smp}$ is the Initial volume of the test solution in ml.; $V_{std}$ is the Initial volume of the standard solution in ml.; $P_{std}$ is the purity of the standard (in decimal form)=% assay as is (from CoA); LC is the label claim; $D_{std}$ is the standard dilution; and $D_{smp}$ is the sample dilution.

Impurities

Instrumentation:

Shimadzu (Duisburg, Germany) Prominence Series HPLC-DAD modular system consisting of a DGU-20A5 mobile phase degasser, an LC-20 AD micro dual piston pump, an SIL-20ACHT autosampler, a CTO-20AC column oven, an SPD-M20 UV/Vis photodiode array detector, and a personal computer with Shimadzu LC Solutions software (v.1.11 SP1) installed for the system control, and the data record and process.

Column:
Kinetex Biphenyl 100A, 250×4.6 mm, 5 µm, Phenomenex (Lot: 5627-0053, P/N: 00G-46270-E0)

REFERENCES

Apixaban Working Standard, Neuland, purity 99.65%, Lot. CS/P/AX/02
Reagents: HPLC-grade water ($H_2O$) (resistivity >18 MΩ cm) by deionization and distillation.
Acetonitrile (ACN) (Carlo Erba, HPLC grade)
Acetic Acid ($CH_3COOH$) (Carlo Erba)
Ammonium Acetate ($CH_3COONH_4$) (LANH: NER)
Dimethyl Sulfoxide (DMSO)
Placebo solution:
Apixaban placebo is stirred, using a magnetic stirrer for 30 minutes. During this period, the placebo is shaken vigorously manually every five minutes. 0.4 ml of apixaban placebo is transferred into a 2 ml glass vial and diluted till 1.0 ml with diluent (final concentration 0.50 mg/ml).
Reference solution of Apixaban (0.001 mg/ml):
Transfer an accurately weighted quantity of Apixaban reference standard of 5.0 mg into a 10 ml volumetric flask. Dilute to volume with diluent, vortex-mix to homogenize. Transfer 0.15 ml of this solution into a 10 ml volumetric flask, dilute to volume with diluent and vortex-mix to homogenize. Further, transfer 1.0 ml of abovementioned solution into a 10 ml volumetric flask and filled up with the same solvent. Prepare two different standard solutions.
Stage-V impurity stock solution (0.5 mg/ml):
Weight accurately 5.0 mg Apixaban Stage-V impurity into a 10 ml volumetric flask, dissolve with diluent and vortex-mix to homogenized. Filled up with the same solvent.
Hydroxyphenyl impurity stock solution (0.5 mg/ml):
Weight accurately 5.0 mg Apixaban Hydroxyphenyl impurity into a 10 ml volumetric flask, dilute to volume with Dimethyl Sulfoxide (DMSO), and vortex-mix to homogenized. Filled up with the same solvent.
Acid impurity stock solution (0.5 mg/ml):
Weight accurately 5.0 mg Apixaban Acid impurity into a 10 ml volumetric flask and filled up with diluent. Vortex-mix to homogenized.
Chloro impurity stock solution (0.5 mg/ml):
Weight accurately 5.0 mg Apixaban Chloro impurity into a 10 ml volumetric flask and filled up with diluent. Vortex-mix to homogenized.
Methyl Ester impurity stock solution (0.5 mg/ml):
Weight accurately 5.0 mg Apixaban Methyl Ester impurity into a 10 ml volumetric flask and dilute to volume with diluent. Vortex-mix to homogenized.
Test solution (0.001 mg/ml):
Apixaban oral solution samples are stirred, using a magnetic stirrer for 30 minutes. During this period, the samples are shaken vigorously manually every five minutes. 0.4 ml of apixaban oral solution are transferred into a 2 ml glass HPLC vial and diluted till 1.0 ml with diluent (final concentration 0.50 mg/ml). 10 µL of the diluted test solution are injected in the HPLC system. Every impurity of the oral solution is quantified using a 0.15% reference solution (one-point calibration).

Chromatographic Parameters
Buffer: Dissolve 2.31 g of ammonium acetate into a 1000 ml HPLC H2O, while stirring. The pH of the solution is adjusted to (4.7+0.05) with acetic acid. The buffer solution is filtered through 0.45 µm filter paper.
Mobile Phase A: Buffer: ACN (80:20) v/v
Mobile Phase B: Buffer: ACN (20:80) v/v. Acidified with 0.5 ml/L acetic acid.

TABLE 5

Gradient Elution

| Time (min) | Mobile Phase A (%) | Mobile Phase B (%) |
|---|---|---|
| 0.01 | 100 | 0 |
| 10.00 | 100 | 0 |
| 20.00 | 60 | 40 |
| 35.00 | 20 | 80 |
| 50.00 | 20 | 80 |
| 55.00 | 100 | 0 |
| 60.00 | 100 | 0 |

Injection volume: 10 µl; flow rate: 0.8 ml/min; column temperature: 20° C.; autosampler temperature: 25° C.; run time: 60 minutes; quantification wavelength: 278 nm.

The retention time of Apixaban and its related substances is presented on Table 6 below:

TABLE 6

Retention times

| Name of Impurity | Retention Time (min) |
|---|---|
| Acid impurity | 17.6 |
| Hydroxyphenyl impurity | 18.5 |
| Apixaban | 21.4 |
| Chloro Impurity | 22.8 |
| Methyl ester impurity | 24.6 |
| Stage - V | 26.1 |

Procedures
Inject three replicates of Apixaban reference solution (before proceeding system suitability criteria should be met). Inject 1 replicate of each sample solution.
System suitability criteria:
Use the 6 replicates of the standard solution:
a) % RSD≤2.0%
b) Tailing Factor≤1.5
c) Plate Count >2000

The % concentration of related substances is calculated based on the following equation:

$$\% \ Rec = \frac{Asmp * Vsmp * Wstd * Pstd * Dstd * 100 * RF}{Astd * Wsmp * LC * Dsmp * Vstd}$$

wherein: $A_{smp}$ is the peak area response of Apixaban active substance in the sample solution chromatogram; $A_{smp}$ ist he peak area response of Apixaban active substance in the sample solution chromatogram; $A_{std}$ is the average peak area response of Apixaban active substance in the standard solution chromatogram; $W_{std}$ is the accurate weight of the Apixaban working standard used for the preparation of the standard solution (mg); $W_{smp}$ is the accurate weigh of the sample used for the preparation of the sample solution (mg);

$V_{smp}$ is the initial volume in ml, of the sample solution; $V_{std}$ is the initial volume in ml, of the standard solution; LC is the label claim; $D_{STD}$ is the standard dilution; $D_{smp}$ is the sample dilution; $P_{std}$ is the % purity of the Apixaban working standard; and RF is the Response Factor=slope of the active substance/slope of impurity.

Stability

Stability tests of formulas 2.1-5 of table 2 are depicted in tables 7-11. The samples were all placed in ICH stability chambers. The humidity was 60% in the tests at 25° C., 65% in the tests at 30° C. and 75% at the tests at 40° C. All formulas fulfil the stability requirements.

Formula 2.4 appears to be stable after even 10 months at 25° C. and 30° C. The results for formula 2.1PS and formula 2.6 (comprising the dispersant polysorbate80) were similar to those of formula 2.1.

TABLE 7

Stability test time zero

| | specs | Form 2.1 | Form 2.1.1 | Form 2.2 | Form 2.3 | Form 2.4 | Form 2.5 | Form 3 | Form 4 | Form 5 |
|---|---|---|---|---|---|---|---|---|---|---|
| assay apixaban | 95.0-105.0% | 97.7 | 100.1 | 102.1 | 98.3 | 101.6 | 98.8 | 105.4 | 98 | 103.1 |
| related substances: | | | | | | | | | | |
| Stage-V | NMT 0.2% | 0.01 | 0.019 | 0.012 | 0.017 | 0.018 | 0.002 | 0.093 | 0.009 | 0.012 |
| Hydroxyphenylimp | NMT 0.2% | | 0.005 | 0.003 | 0.002 | 0.001 | | | | |
| Acid Impurity | NMT 0.2% | | 0.01 | 0.02 | 0.019 | 0.028 | | 0.009 | | 0.013 |
| Chloro impurity | NMT 0.2% | | 0.001 | 0.002 | 0.001 | 0.005 | | | | |
| Methyl ester imp | NMT 0.2% | | | | | | 0.04 | | | |
| Any unspecified impurity | NMT 0.1% | | | | | | | | | |
| Total Impurities | NMT 2% | 0.01 | 0.035 | 0.037 | 0.039 | 0.052 | 0.042 | 0.102 | 0.009 | 0.025 |

TABLE 8

Stability test time 3 M - 25 C./60 RH %

| | specs | Form 2.1 | Form 2.1.1 | Form 2.2 | Form 2.3 | Form 2.4 | Form 2.5 | Form 3 | Form 4 | Form 5 |
|---|---|---|---|---|---|---|---|---|---|---|
| assay apixaban | 95.0-105.0% | 96.7 | 97.6 | 98.3 | 100.9 | 99 | 98 | 102.6 | 100 | 96.8 |
| related substances: | | | | | | | | | | |
| Stage-V | NMT 0.2% | 0.03 | 0.04 | 0.03 | 0.03 | 0.03 | 0.01 | 0.03 | 0.03 | 0.02 |
| Hydroxyphenylimp | NMT 0.2% | 0.002 | 0.001 | 0.002 | 0.002 | 0.002 | | 0.0003 | | 0.001 |
| Acid Impurity | NMT 0.2% | 0.01 | 0.01 | 0.39 | 0.109 | 0.063 | 0.01 | 0.01 | 0.01 | 0.01 |
| Chloro impurity | NMT 0.2% | 0.001 | 0.002 | | | 0.01 | | | | |
| Methyl ester imp | NMT 0.2% | 0.003 | 0.003 | 0.005 | 0.005 | 0.01 | 0.09 | 0.0002 | | 0.001 |
| Any unspecified impurity | NMT 0.1% | | | | | | | | | |
| Total Impurities | NMT 2% | 0.046 | 0.056 | 0.427 | 0.146 | 0.115 | 0.11 | 0.0405 | 0.04 | 0.032 |

TABLE 9

Stability test time 3 M - 30 C./65 RH %

| | specs | Form 2.1 | Form 2.1.1 | Form 2.2 | Form 2.3 | Form 2.4 | Form 2.5 | Form 3 | Form 4 | Form 5 |
|---|---|---|---|---|---|---|---|---|---|---|
| assay apixaban | 95.0-105.0% | 96.2 | 95.4 | 98.1 | 96.8 | 98.5 | 99.1 | 101.6 | 95 | 94.5 |
| related substances: | | | | | | | | | | |
| Stage-V | NMT 0.2% | 0.033 | 0.039 | 0.034 | 0.03 | 0.03 | 0.01 | 0.04 | 0.031 | 0.025 |
| Hydroxyphenylimp | NMT 0.2% | | 0.003 | 0.001 | | | | | 0.001 | 0.001 |
| Acid Impurity | NMT 0.2% | | | 0.18 | 0.05 | 0.072 | 0.002 | 0.002 | 0.002 | 0.004 |
| Chloro impurity | NMT 0.2% | | | | | 0.01 | | | | |
| Methyl ester imp | NMT 0.2% | 0.001 | 0.009 | 0.01 | 0.01 | 0.01 | 0.08 | | 0.001 | 0.002 |
| Any unspecified impurity | NMT 0.1% | | | | | | | | | |
| Total Impurities | NMT 2% | 0.034 | 0.051 | 0.225 | 0.09 | 0.122 | 0.092 | 0.042 | 0.035 | 0.032 |

TABLE 10

Stability test
time 3 M - 40 C./75 RH %

| | specs | Form 2.1 | Form 2.1.1 | Form 2.2 | Form 2.3 | Form 2.4 | Form 2.5 | Form 3 | Form 4 | Form 5 |
|---|---|---|---|---|---|---|---|---|---|---|
| assay apixaban | 95.0-105.0% | 96.9 | 95.3 | 100.4 | 96.2 | 100.5 | 102.5 | 97.9 | 94.1 | 94.5 |
| related substances: | | | | | | | | | | |
| Stage-V | NMT 0.2% | 0.027 | 0.029 | 0.03 | 0.025 | 0.029 | 0.01 | 0.03 | 0.023 | 0.024 |
| Hydroxyphenylimp | NMT 0.2% | | 0.001 | 0.01 | | | 0.001 | 0.001 | 0.001 | 0.001 |
| Acid Impurity | NMT 0.2% | 0.011 | 0.006 | 0.16 | 0.145 | 0.104 | | | 0.006 | 0.008 |
| Chloro impurity | NMT 0.2% | | | | | 0.003 | | | | |
| Methyl ester imp | NMT 0.2% | 0.072 | 0.009 | | 0.006 | 0.007 | 0.072 | 0.005 | 0.003 | 0.001 |
| Any unspecified impurity | NMT 0.1% | | | | | | | | | |
| Total Impurities | NMT 2% | 0.11 | 0.045 | 0.2 | 0.176 | 0.143 | 0.083 | 0.036 | 0.033 | 0.034 |

TABLE 11

Stability test
time 3 M - 5 C./no HUMIDITY

| | specs | Form 2.1 | Form 2.1.1 | Form 2.2 | Form 2.3 | Form 2.4 | Form 2.5 | Form 3 | Form 4 | Form 5 |
|---|---|---|---|---|---|---|---|---|---|---|
| assay apixaban | 95.0-105.0% | 94.5 | 95 | 97.7 | 99.1 | 98.2 | 96.9 | 95.1 | 92.2 | 92.4 |
| related substances: | | | | | | | | | | |
| Stage-V | NMT 0.2% | 0.05 | 0.06 | 0.04 | 0.02 | 0.04 | 0.02 | 0.03 | 0.04 | 0.03 |
| Hydroxyphenylimp | NMT 0.2% | 0.003 | 0.01 | | 0.001 | 0.003 | 0.001 | 0.001 | 0.002 | 0.001 |
| Acid Impurity | NMT 0.2% | 0.04 | 0.03 | 0.21 | 0.07 | 0.05 | 0.02 | 0.01 | 0.01 | 0.02 |
| Chloro impurity | NMT 0.2% | 0.01 | 0.005 | 0.01 | 0.001 | 0.01 | | | | |
| Methyl ester imp | NMT 0.2% | 0.01 | | | 0.01 | 0.01 | 0.11 | 0.004 | 0.003 | 0.003 |
| Any unspecified impurity | NMT 0.1% | | | | | | | | | |
| Total Impurities | NMT 2% | 0.113 | 0.105 | 0.26 | 0.102 | 0.113 | 0.151 | 0.045 | 0.015 | 0.054 |

TABLE 12

Stability test

| | specs | time 10 M 25 C./ 60 RH % | time 10 M 30 C./ 60 RH % |
|---|---|---|---|
| | | Formula 2.4 | |
| assay apixaban | 95.0-105.0% | 99.2 | 101.8 |
| related substances: | | | |
| Stage-V | NMT 0.2% | | |
| Hydroxyphenylimp | NMT 0.2% | | |
| Acid Impurity | NMT 0.2% | 0.06 | 0.067 |
| Chloro impurity | NMT 0.2% | | |
| Methyl ester imp | NMT 0.2% | | |
| Any unspecified impurity | NMT 0.1% | | |
| Total Impurities | NMT 2% | 0.06 | 0.067 |

Dissolution tests

The dissolution test were performed in compliance with the European Pharmacopeia 10.0, section 2.9.3

Instrumentation:

Shimadzu (Duisburg, Germany) Prominence Series HPLC-DAD modular system consisting of a DGU-20A5 mobile phase degasser, an LC-20 AD micro dual piston pump, an SIL-20ACHT autosampler, a CTO-20AC column oven, an SPD-M20 UV/Vis photodiode array detector, and a personal computer with Shimadzu LC Solutions software (v.1.11 SP1) installed for the system control, and the data record and process.

Column:
Zorbax Eclipse XDB-C8, 150×4.6 mm, 5 μm
References: Apixaban Working Standard
Reagents:
HPLC-grade water (resistivity >18 MΩ cm) by deionization and distillation.
Acetonitrile (ACN) (Carlo Erba, HPLC grade)
Acetic Acid ($CH_3COOH$) (Carlo Erba)
Ammonium Acetate ($CH_3COONH_4$) (LANH: NER)
Hydrochloric Acid (Fisher Chemical)
Sodium Hydroxide (LACH: NER)
Diluent:
ACN: $H_2O$ (50:50) v/v.
Buffers:
PH 1.5: HCl 0.1N. Transfer 42.5 ml Hydrochloric acid 37% v/v and 1000 ml $H_2O$ in a beaker and stir.
pH 4.5: Weigh 13.61 g potassium phosphate monobasic into 1000 ml $H_2O$, stir until completely dilution.
pH 6.8: Weigh 1 g sodium hydroxide into 125 ml $H_2O$. Then, weigh 6.8 g potassium dihydrogen phosphate into 250 ml $H_2O$ (0.2M). Transfer 112 ml sodium hydroxide solution and 250 ml 0.2M potassium dihydrogen phosphate solution and filled up with $H_2O$ until 1000 ml.
Standard solution of Apixaban (0.005 mg/ml):
Transfer an accurately weighted quantity of Apixaban reference standard of 5.0 mg into a 10 ml volumetric flask. Dilute to volume with diluent, vortex-mix to homogenize. Transfer 0.1 ml of this solution into a 10 ml volumetric flask, dilute to volume with dissolution medium and vortex-mix to homogenize. Prepare two different standard solutions.

Test solution (0.005 mg/ml):
Transfer individually 900 ml of dissolution medium into six dissolution vessels. After the temperature has reached 37+0.5° C., insert 4.0 ml of Apixaban oral solution 1.25 mg/ml, into each vessel, cover, and start the rotation. Use the puddles and 50 rpm for the rotation. After 30 minutes of dissolution's time point, an aliquot of 5 ml of the solution is removed from each vessel. Transfer in an HPLC vial.

Chromatographic Parameters:
Mobile Phase A: Dissolve 2.31 g/l of ammonium acetate into $H_2O$. Adjust pH to 4.7 with acetic acid.
Mobile Phase B: ACN: $H_2O$ (90:10) v/v. final acidified with 1 ml acetic acid.

TABLE 13

| | Gradient | |
|---|---|---|
| Time (min) | Mobile Phase A (%) | Mobile Phase B (%) |
| 0.01 | 55 | 45 |
| 5.0 | 55 | 45 |
| 10.0 | 20 | 80 |
| 12.0 | 55 | 45 |
| 20.0 | 55 | 45 |

Injection volume: 10 μl; flow rate: 0.8 ml/min; column temperature: 20° C.; autosampler temperature: 25° C.; run time: 20 minutes; quantification wavelength: 240 nm; retention time of apixaban: 3.5 min.

Procedures
Inject six replicates of Apixaban standard solution (before proceeding system suitability criteria should be met) and 2 replicates of verification standard solution. Calculate the recovery against the mean areas of the two standard solutions. (The recovery should be between 98-102%). Inject 1 replicate of each sample solution.

System suitability criteria:
Use the 6 replicates of the standard solution:
a) % RSD≤2.0%
b) Tailing Factor≤1.8
c) Plate Count >2000

The % content of Apixaban is calculated based on the following equation:

$$\% \text{ Content} = \frac{Atest \times Wstd \times Pstd \times Dstd \times Vtest \times 100}{Astd \times Wtest \times LC \times Vstd}$$

wherein $A_{test}$ is the peak area response of Apixaban in the sample solution chromatogram; $A_{std}$ is the Average peak area response of Apixaban in the standard solution chromatogram; $W_{std}$ is the accurate weigh of the Apixaban working standard used for the preparation of the standard solution (mg); $W_{test}$ is the ml of the sample transferred in each dissolution vessel; $V_{test}$ is the Initial volume in ml, of the dissolution medium in the vessels; $V_{std}$ is the Initial volume in ml, of the standard solution; $D_{std}$ is the dilution of the standard; LC is the Label claim (0.4 mg/ml); $P_{std}$ is the % purity of the Apixaban working standard.

The dissolution profiles of formula 2.1 and of Eliquis are shown in table 14. The values are averages of 5 measurements with a maximum standard deviation of 3%. At time 0, all suspensions perform better than Eliquis. In time, in particular at 30° C., the dissolution rate of the suspension samples is better than those for Eliquis at pH 4.5. Sample 2.4 performs best at all pH values tested.

TABLE 14

| | | | | | dissolution profiles time zero | | | | | |
|---|---|---|---|---|---|---|---|---|---|---|
| | Dissolution % - Formula 2.1 | | | Dissolution % - Formula 2.4 | | | Dissolution % - Eliquis 5 mg | | | |
| t (min) | pH 1.5 | pH 4.5 | pH 6.8 | t (min) | pH 1.5 | pH 4.5 | pH 6.8 | t (min) | pH 1.5 | pH 4.5 | pH 6.8 |
| 10 | 101.1 | 90.9 | 101.1 | 10 | 100.5 | 91.0 | 100.2 | 10 | 58.3 | 54.2 | 72.6 |
| 15 | 105.3 | 94.7 | 105.3 | 15 | 104.8 | 95.0 | 104.3 | 15 | 80.2 | 81.8 | 90.8 |
| 20 | 106.7 | 94.7 | 106.7 | 20 | 105.2 | 96.5 | 105.9 | 20 | 89.1 | 91.1 | 96.6 |
| 30 | 109.6 | 97.2 | 109.6 | 30 | 107.2 | 96.4 | 107.5 | 30 | 99.6 | 100.2 | 101.8 |
| 45 | 112.3 | 98.5 | 112.3 | 45 | 109.2 | 99.5 | 108.5 | 45 | 106.0 | 105.9 | 107.6 |
| 60 | 113.9 | 100.7 | 113.9 | 60 | 109.0 | 101.1 | 109.2 | 60 | 109.7 | 109.5 | 110.0 |
| | | | | | 6 months at 25 C. | | | | | | |
| 10 | 36.8 | 48.0 | 51.5 | 10 | 45.5 | 45.0 | 62.2 | 10 | 50.2 | 50.2 | 68.2 |
| 15 | 39.3 | 54.4 | 56.4 | 15 | 66.2 | 68.0 | 85.0 | 15 | 75.5 | 78.8 | 88.0 |
| 20 | 41.0 | 57.0 | 59.3 | 20 | 85.2 | 85.2 | 88.2 | 20 | 88.2 | 88.5 | 92.0 |
| 30 | 43.4 | 61.5 | 63.5 | 30 | 90.1 | 97.0 | 97.2 | 30 | 99.1 | 99.2 | 99.2 |
| 45 | 45.3 | 66.7 | 67.4 | 45 | 105.2 | 99.0 | 102.2 | 45 | 105.2 | 104.2 | 105.1 |
| 60 | 48.5 | 69.4 | 70.7 | 60 | 106.0 | 100.5 | 104.1 | 60 | 108.2 | 107.2 | 108.2 |
| | | | | | 10 months at 25 C. | | | | | | |
| 10 | | | 50.2 | 10 | | | 58.6 | 10 | | | 65.2 |
| 15 | | | 54.2 | 15 | | | 70.2 | 15 | | | 87.1 |
| 20 | | | 58.4 | 20 | | | 80.2 | 20 | | | 90.1 |
| 30 | | | 60.2 | 30 | | | 90.1 | 30 | | | 98.5 |
| 45 | | | 65.4 | 45 | | | 104.8 | 45 | | | 102.1 |
| 60 | | | 69.1 | 60 | | | 108.6 | 60 | | | 105.1 |
| | | | | | 6 months at 30 C. | | | | | | |
| 10 | 25.1 | 42.2 | 28.0 | 10 | 42.2 | 44.1 | 55.5 | 10 | 28.5 | 32.9 | 33.8 |
| 15 | 30.2 | 48.6 | 32.4 | 15 | 64.3 | 65.2 | 70.2 | 15 | 35.2 | 41.9 | 40.9 |
| 20 | 38.1 | 55.0 | 35.5 | 20 | 85.0 | 85.2 | 75.6 | 20 | 40.1 | 44.9 | 44.1 |

TABLE 14-continued

| dissolution profiles time zero | | | | | | | | | | |
|---|---|---|---|---|---|---|---|---|---|---|
| Dissolution % - Formula 2.1 | | | | Dissolution % - Formula 2.4 | | | | Dissolution % - Eliquis 5 mg | | |
| t (min) | pH 1.5 | pH 4.5 | pH 6.8 | t (min) | pH 1.5 | pH 4.5 | pH 6.8 | t (min) | pH 1.5 | pH 4.5 | pH 6.8 |
| 30 | 38.1 | 59.1 | 40.0 | 30 | 88.1 | 96.5 | 85.2 | 30 | 42.3 | 47.0 | 46.6 |
| 45 | 40.2 | 60.2 | 44.3 | 45 | 104.1 | 98.8 | 100.2 | 45 | 45.2 | 49.5 | 48.9 |
| 60 | 45.1 | 60.1 | 47.6 | 60 | 104.9 | 100.2 | 102.2 | 60 | 46.2 | 51.2 | 50.4 |
| 10 months at 30 C. | | | | | | | | | | | |
| 10 | | | 25.2 | 10 | | | 52.2 | 10 | | | 30.5 |
| 15 | | | 28.2 | 15 | | | 68.9 | 15 | | | 39.1 |
| 20 | | | 33.2 | 20 | | | 78.6 | 20 | | | 40.1 |
| 30 | | | 38.5 | 30 | | | 86.2 | 30 | | | 42.2 |
| 45 | | | 42.1 | 45 | | | 105.2 | 45 | | | 45.1 |
| 60 | | | 44.6 | 60 | | | 109.5 | 60 | | | 48.2 |

Further, it was observed that formula 2.4 had a solubility after 45 minutes of 108.6% and 109.5 after being stored for 10 months at 25° C. at a humidity of 60%, and at 30° C. at a humidity of 65%, respectively.

Form stability

The form stability was tested by X-ray powder diffraction analysis.

Sample Preparation

Dry powder reference samples (apixaban raw material from Neuland, Amino and Teva) were loaded in a standard sample holder and evenly spread with the help of a glass slide. Formula 2.1-5 suspensions were shaken well and the suspension was transferred in a 50 ml falcon tube. The suspension was centrifuged at 8,000 rpm, 25° C. for 23 minutes (Heraeus Biofuge Stratos). The precipitate was isolated, loaded in a Si low background sample holder, dried at ambient temperature and the XRD pattern was recorded with a Bruker D2 Phaser or Bruker D2 Phaser XE-T Edition with the following settings:

Source: Cu κα (λ=1.54° A)
Detector type: LynxEye or LynxEye XE-T
Primary Divergence slit: 0.6 mm
Antiscatter slit: 8.0 mm
Soler slit: 2.5°
Air scatter screen: 3 mm
PSD-Opening: 5°
Voltage: 30 kV
Current: 10 mA
Rotation: 0 rpm
Background removal: Yes
Start angle: 2 2-theta
End angle: 40 2-theta
Step size: 0.02 2-theta
Scanning rate: 2.0 s/step
Scan type: Locked Coupled
Scan mode: Continuous
Sample holder: Si low background sample holder with a 25 mm diameter and 0.5 mm depth circular cavity for spreading the sample
Glass slides: 25×75×1 mm glass slides The suspension samples were kept at 5°° C. or 25° C. and 60% humidity for 9 months, and compared with fresh samples of batches directly obtained from the manufacturer and with a fresh sample of Eliquis (5 mg tablet, lot DX2023). The crystal forms in the samples were identified based on the obtained XRD patterns and depicted in FIGS. 1-9. On the X axis, the angle 2θ° is given, and the Y-axis shows the intensity % of the counts, the highest peak corresponding with 100%. The obtained patterns were compared with patterns known from the above literature to evaluate the crystal form.

The crystal forms as identified are listed in table 15.

TABLE 15

| XRD patterns | | |
|---|---|---|
| Apixaban sample | Apixaban form | FIG. |
| Neuland Labs | I | 1 |
| Amino Chemicals | I | 2 |
| Eliquis | I | 3 |
| Eliquis (25° C.) | I | 4 |
| Eliquis (40° C.) | I + VIII | 5 |
| Formula 2.1 (25° C.) | VIII | 6 |
| Formula 2.1PS (30° C.) | VIII | |
| Formula 2.1.1 (5° C.) | Unknown | |
| Formula 2.2 (5° C.) | I + VIII | |
| Formula 2.3 (5° C.) | VIII | |
| Formula 2.3 (25° C.) | VIII | 7 |
| Formula 2.4 (5° C.) | I | 8 |
| Formula 2.4 (25° C.) | I | 9 |
| Formula 2.5 (5° C.) | Unknown | |
| Formula 2.5 (25° C.) | VIII | |
| Formula 2.6 (25° C.) | VIII | |

The raw materials from the manufacturers as well as the apixaban from Eliquis tablets all have crystal form I. It is observed that the reference material Eliquis underwent a conformational change from crystal form 1 to form Vill when stored at 40° C. Similar conformational changes are observed for samples having a relatively high pH of 5.5-6.5 when kept at 25° C. Samples having a pH of below 5.5, i.e. samples of formula 2.4 remain the crystal form 1 throughout storage.

Stability comparison

Sample 2.4 in strengths of 0.6 mg/ml and 1.25 mg/ml, as well as nanosuspensions of the same strength, prepared according to example 7 of CN109010273A were prepared and subjected to the stability test as explained above, under force conditions of 40° C. and 75% RH. It is observed that for both strengths, the suspension of the invention is more stable as compared to the nanosuspension of example 7 of the Chinese document, see table 16.

TABLE 16

Comparative stability test
time 0-1 M - 40 C./75 RH %

| | specs | CN Ex 7 - 0.6 mg/ml 0 M | CN Ex 7 - 0.6 mg/ml 1 M | CN Ex 7 - 1.25 mg/ml 0 M | CN Ex 7 - 1.25 mg/ml 1 M | Sample 2.4 0.6 mg/ml 0 M | Sample 2.4 0.6 mg/ml 1 M | Sample 2.4 1.25 mg/ml 0 M | Sample 2.4 1.25 mg/ml 1 M |
|---|---|---|---|---|---|---|---|---|---|
| Density | 1.00-1.05 | 1.00 | 1.00 | 1.00 | 1.00 | 1.00 | 1.00 | 1.00 | 1.00 |
| assay apixaban | 95.0-105.0% | 97.1% | 96.1% | 91.0% | 90.8% | 90.9% | 90.5% | 92.9% | 92.5% |
| related substances: | | | | | | | | | |
| Acid Impurity | NMT 0.2% | BRT | 0.10% | BRT | 0.10% | BRT | BRT | BRT | BRT |
| Any unspecified impurity | NMT 0.1% | BRT | BRT | BRT | BRT | BR | BRT | BRT | BRT |
| Total Impurities | NMT 2% | BRT | 0.10% | BRT | 0.10% | BRT | BR | BRT | BRT |

Particle size distribution

Sample 2.4 was prepared on industrial scale in a volume of 200L, as described above for the laboratory scale preparations. Homogenisation was performed in an industrial rotor-stator homogeniser with a 5.5 kW engine power (Vasilakakos, Greece) for 60 minutes at 500-1.500 rpm.

The particle size was calculated using a particle size analyser (Malvern Panalytical Ltd. UK).

Figure 10:
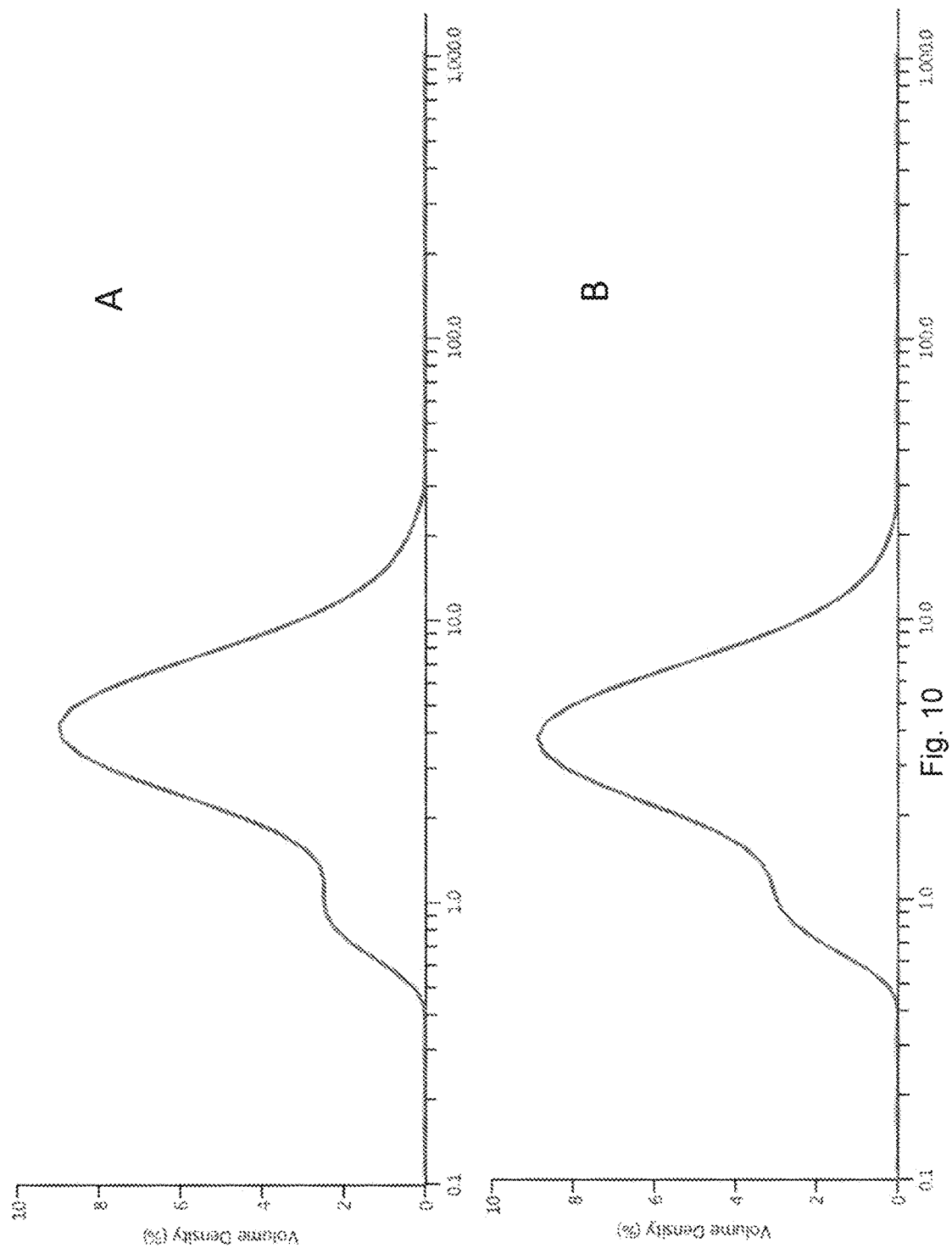

The particle size did not significantly change after the second round of homogenisation (2H), see table 17 and FIGS. 10A and B, showing the particle size distribution after one (1H) and two rounds (2H) of homogenisation, respectively.

TABLE 17 particle size in μm

| | 1H | 2H |
|---|---|---|
| $D_{10}$ | 1.18 | 1.09 |
| $D_{50}$ | 3.79 | 3.36 |
| $D_{90}$ | 8.71 | 7.70 |
| $D_{[4, 3]}$ | 4.47 | 4.04 |

Particle observation

Observation of a suspension of sample 2.4 in a strength of 1.25 mg/ml was performed with a Leica DM 2500 M Microscope equipped with a digital camera (DFC 420C, 10x). Sample preparation: one drop of the suspension sample was placed on an object glass, covered with a cover slip and viewed under the microscope using 5x, 10x, 20x and 40x lens. Respective fields were captured. Mode: Transmittance, Sample 1) Apixaban Oral Suspension 1.25 mg/ml once homogenized, and sample 2) Apixaban Oral Suspension 1.25 mg/ml homogenized twice.

Figure 11A:
Figure 11A:
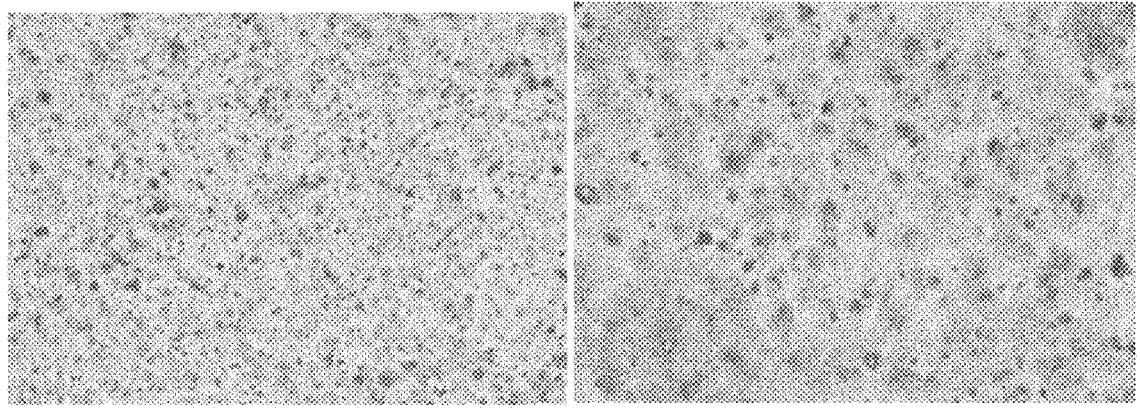

After a single homogenization, the majority of independent particles are small (1-4 μm). In rare occasions there have been observed bigger independent particles (~10 μm). Aggregates, varying in size from small clusters of a few particles of 5-10 μm (mainly observed), to rarely found aggregates of 20-50 μm, see FIG. 11A.

Figure 11B:
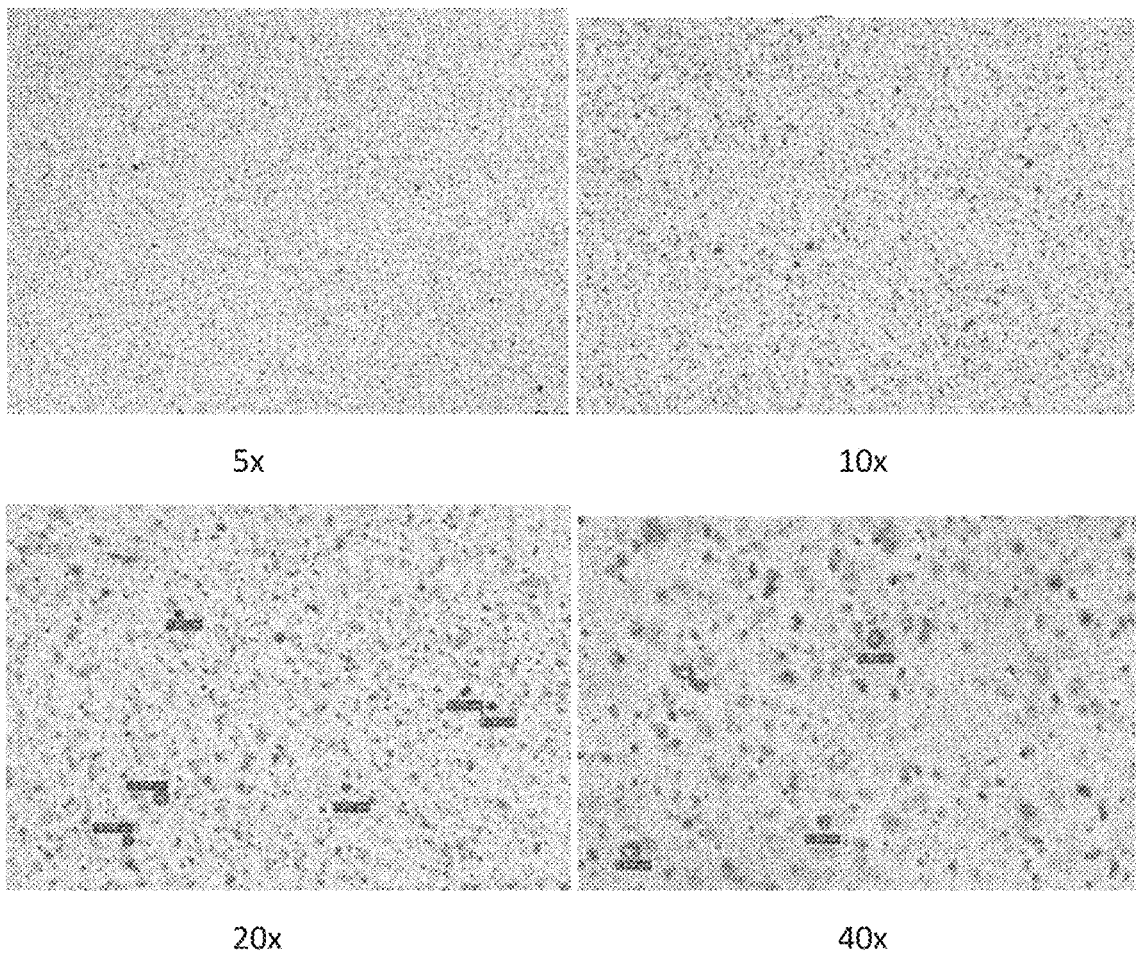

After twice homogenization, the majority of independent particles is small (1-4 μm). In very rare occasions there have been observed larger independent particles (~10 μm). Aggregates have been observed, varying in size from small clusters of a few particles 5-10 μm (mainly observed), to 20-30 μm. Larger aggregates have not been observed, see FIG. 11B.

Microbial Efficacy

Formula 2.4 was tested for efficacy of antimicrobial preservation according to the teaching of the European Pharmacopeia 9.0, section 5.1.3, pp 577 ff. by Quality Assurance & Control Systems Ltd., Athens, Greece. The test consists of challenging the sample solution with a prescribed inoculum of suitable micro-organisms as shown in the table 18, storing the inoculated solution at ambient temperature, avoiding sunlight, withdrawing samples from the container at specified intervals of time and counting the micro-organisms in the samples so removed. The preservative properties of the solution are adequate if, in the conditions of the test, there is a significant fall or no increase, as appropriate, in the number of micro-organisms in the inoculated solution after 14 and 28 days. ATCC stands for the deposit number of the micro-organism at the American Type Culture Collection ATCC.

TABLE 18

Microbial efficacy sample 2.4

| Micro-organism | ATCC | Lot | Inoculation Cfu/g | Time zero |
|---|---|---|---|---|
| *Pseudomonas aeruginosa* | 9027 | 48412452 | $4.4 \times 10^5$ | $4.2 \times 10^5$ |
| *Staphylococcus aureus* | 6538 | 4854821 | $5.2 \times 10^5$ | $5.3 \times 10^5$ |
| *Escherichia coli* | 8739 | 4835664 | $6.6 \times 10^5$ | $6.6 \times 10^5$ |
| *Candida albicans* | 10231 | 4435903 | $3.6 \times 10^5$ | $4.0 \times 10^5$ |
| *Aspergillus brasiliensis* | 16404 | 3929552 | $3.4 \times 10^5$ | $2.8 \times 10^5$ |

The invention claimed is:

1. A buffered oral aqueous apixaban suspension comprising a buffering agent and 0.08-0.20 w/v % micronized apixaban having a pH of 1.5-6.5, the suspension being void of emulsifier and surfactant.

2. The buffered oral aqueous apixaban suspension of claim 1,
wherein the apixaban particles in the suspension have a D10 of at least 1.0 μm.

3. The buffered oral aqueous apixaban suspension of claim 1,
wherein the apixaban particles in the suspension have a D90 of 20 μm or less.

4. The buffered oral aqueous apixaban suspension of claim 1,
comprising 0.10-0.15 w/v % apixaban.

5. The buffered oral aqueous apixaban suspension of claim 1,
wherein at least 95% w/w % of the apixaban present in the suspension is in crystalline Form I.

6. The buffered oral aqueous apixaban suspension of claim 1, comprising at least 80 w/v % water.

7. The buffered oral aqueous apixaban suspension of claim 1, wherein said buffering agent is selected from the group consisting of acetic acid, ammonia solutions, monoethanolamine, diethanolamine, triethanolamine, meglumine, sodium citrate, citric acid, lactic acid, phosphoric acid, propionic acid, sulphuric acid, tartaric acid, potassium bicarbonate, potassium citrate, potassium hydroxide, sodium bicarbonate, sodium borate, sodium hydroxide, and combinations thereof.

8. The buffered oral aqueous apixaban suspension of claim 7, the buffering agent comprising citric acid and a citrate salt, in an amount of 0.05-2.0 w/v %.

9. The buffered oral aqueous apixaban suspension of claim 1, comprising one or more thickening agents, the one or more thickening agents being chosen from the group, consisting of xanthan gum, acacia, guar gum, locust bean gum, gum tragacanth, gellan gum, hydroxyethyl cellulose, hydroxypropyl cellulose, sodium alginate, sodium carboxy methylcellulose, starch, carbopols, methylcellulose, polyethylene oxide polymer and combinations thereof.

10. The buffered oral aqueous apixaban suspension of claim 9, the one or more thickening agents comprising xanthan gum in an amount of 0.20-0.30 w/v %.

11. The buffered oral aqueous apixaban suspension of claim 1, further comprising one or more preservatives, chosen from the group, consisting of benzoic acid, sodium benzoate, potassium sorbate, benzyl benzoate, benzalkonium chloride, benzethonium chloride, boric acid and salts thereof, cetrimide, chlorocresol, thimerosal, imidurea, glycerine, monothioglycerol, propylene glycol, propionic acid and salts thereof, acetic acid and salts thereof, lactic acid and salts thereof, alkyl acids and salts thereof, pentetic acid and salts thereof, sodium sulphite, sodium metabisulphite, benzyl alcohol, ethylalcohol, potassium sorbate, methyl paraben, ethyl paraben, propyl paraben, butyl paraben, and combinations thereof.

12. The buffered oral aqueous apixaban suspension of claim 11, wherein the one or more preservatives comprise benzoic acid or sodium benzoate, or a combination thereof, in an amount of 0.02-0.10 w/v %.

13. The buffered oral aqueous apixaban suspension of claim 1, comprising one or more antioxidants, chosen from the group, consisting of sodium metabisulphite, sodium sulphite, sodium thiosulfate, propyl gallate, butylated hydroxyl anisole, butylated hydroxyl toluene, tocopherol, ascorbyl palmitate, ascorbic acid and combinations thereof.

14. The buffered oral aqueous apixaban suspension of claim 1, comprising one or more sweetening agents, the amount of the one or more sweetening agents in the composition having a sweetening power that corresponds with the sweetening power of 60-600 w/v % saccharose.

15. The buffered oral aqueous apixaban suspension of claim 1, comprising one or more sweetening agents in an amount of 0.1-10 w/v %.

16. The buffered oral aqueous apixaban suspension of claim 1, comprising one or more artificial sweetening agents, chosen from the group consisting of sucralose, sodium saccharin, aspartame, alitame, acesulfame-K, cyclamate, stevioside, glycyrrhizin, neohesperidin, dihydrochalcone, thaumatin, and combinations thereof.

17. The buffered oral aqueous apixaban suspension of claim 16, wherein the one or more sweetening agents comprise sucralose and sodium saccharin, in an amount of 0.3-1.0 w/v %, the weight ratio between sucralose and sodium saccharin being 1:0.3-0.5.

18. The buffered oral aqueous apixaban suspension of claim 1, further comprising one or more flavouring agents, selected from the group consisting of peppermint, spearmint, *eucalyptus*, vanilla, forest fruits flavour, grapefruit, orange, lime, lemon, mandarin, pineapple, strawberry, raspberry, mango, passion fruit, kiwi, apple, pear, peach, apricot, cherry, grapes, banana, cranberry, blueberry, black currant, red currant, gooseberry, lingonberries, cumin, thyme, basil, camomile, valerian, fennel, parsley, tarragon, lavender, dill, bergamot, *salvia*, aloe vera balsam and combinations of two or more thereof.

19. The buffered oral aqueous apixaban suspension of claim 1, wherein at least 98 w/w % of the solid form of apixaban in the suspension, is in crystalline Form I, and is still present after storage of 30 ml of the suspension for 10 months in a closed 30 ml amber glass vial at 25° C., 60% humidity in the dark.

20. A method for the preparation of the buffered oral aqueous apixaban suspension of claim 1, comprising the steps of:

(i) providing purified water,
(ii) if present, admixing the preservative,
(iii) if present, admixing the sweeteners
(iv) if present, admixing the antioxidant,
(v) if present, a chelating agent,
(vi) admixing the pH buffer agent,
(vii) if present, admixing the flavour,
(viii) admixing the apixaban to the mixture of steps (i)-(vii) and homogenizing,
(ix) if present, admixing the thickener and homogenizing,
(x) if present, admixing the co-solvent,
(xi) if necessary, adjusting pH at 1.5-6.5 with ingredients of step (v),
(xii) if necessary, adjusting to the final volume by adding purified water,
(xiii) optionally, filtering through a 10 μm pore sieve or higher, and
(xiv) filling into an appropriate container.

* * * * *